United States Patent
Benz et al.

(10) Patent No.: US 9,924,949 B2
(45) Date of Patent: Mar. 27, 2018

(54) VASCULAR COMPRESSION APPARATUS, PAD AND METHOD OF USE

(75) Inventors: Philip Benz, Portland, OR (US); Robert Niemeyer, Tigard, OR (US)

(73) Assignee: Semler Technologies, Inc., Milwaukie, OR (US)

(*) Notice: Subject to any disclaimer, the term of this patent is extended or adjusted under 35 U.S.C. 154(b) by 337 days.

(21) Appl. No.: 12/737,087

(22) PCT Filed: Oct. 30, 2009

(86) PCT No.: PCT/US2009/005892
§ 371 (c)(1),
(2), (4) Date: Feb. 10, 2011

(87) PCT Pub. No.: WO2010/056280
PCT Pub. Date: May 20, 2010

(65) Prior Publication Data
US 2012/0053617 A1  Mar. 1, 2012

Related U.S. Application Data

(60) Provisional application No. 61/198,956, filed on Nov. 12, 2008.

(51) Int. Cl.
*A61B 17/00* (2006.01)
*A61B 17/132* (2006.01)

(52) U.S. Cl.
CPC ...... *A61B 17/1325* (2013.01); *A61B 17/1327* (2013.01); *A61B 2017/00889* (2013.01)

(58) Field of Classification Search
USPC .......................................... 606/203
See application file for complete search history.

(56) References Cited

U.S. PATENT DOCUMENTS

| | | | | |
|---|---|---|---|---|
| 2,604,098 A * | 7/1952 | Kranc | ............. | 606/203 |
| 4,760,846 A * | 8/1988 | Mers Kelly | ........ | A61B 17/1325 606/158 |
| 4,909,051 A * | 3/1990 | Lee | .......... | E05B 75/00 128/878 |
| 5,269,803 A * | 12/1993 | Geary | ............... | A61B 17/1322 606/201 |
| 6,398,596 B1 * | 6/2002 | Malin | ............. | 439/800 |
| 7,096,543 B2 * | 8/2006 | Castellanos | ................. | 24/16 PB |
| 9,127,486 B2 * | 9/2015 | Liang | .................. | E05B 65/0894 |
| 2005/0267518 A1 * | 12/2005 | Wright | ................. | A61B 17/132 606/203 |

FOREIGN PATENT DOCUMENTS

GB     2027149 A  *  2/1980

* cited by examiner

*Primary Examiner* — Amy R Weisberg

(57) ABSTRACT

An adjustable vascular compression device assists in achieving partial or full occlusion of a blood vessel when applied to a patient's limb, for example, during or following a medical procedure. Pads on the device apply preferential compression to portions of the circumference of the limb so as to enable blood flow through adjacent blood vessels during the compression period. Further, rapid fastening, tightening, loosening and release is enabled by a single mechanism, and gradual adjustments to the tightness may be made without releasing said mechanism.

6 Claims, 12 Drawing Sheets

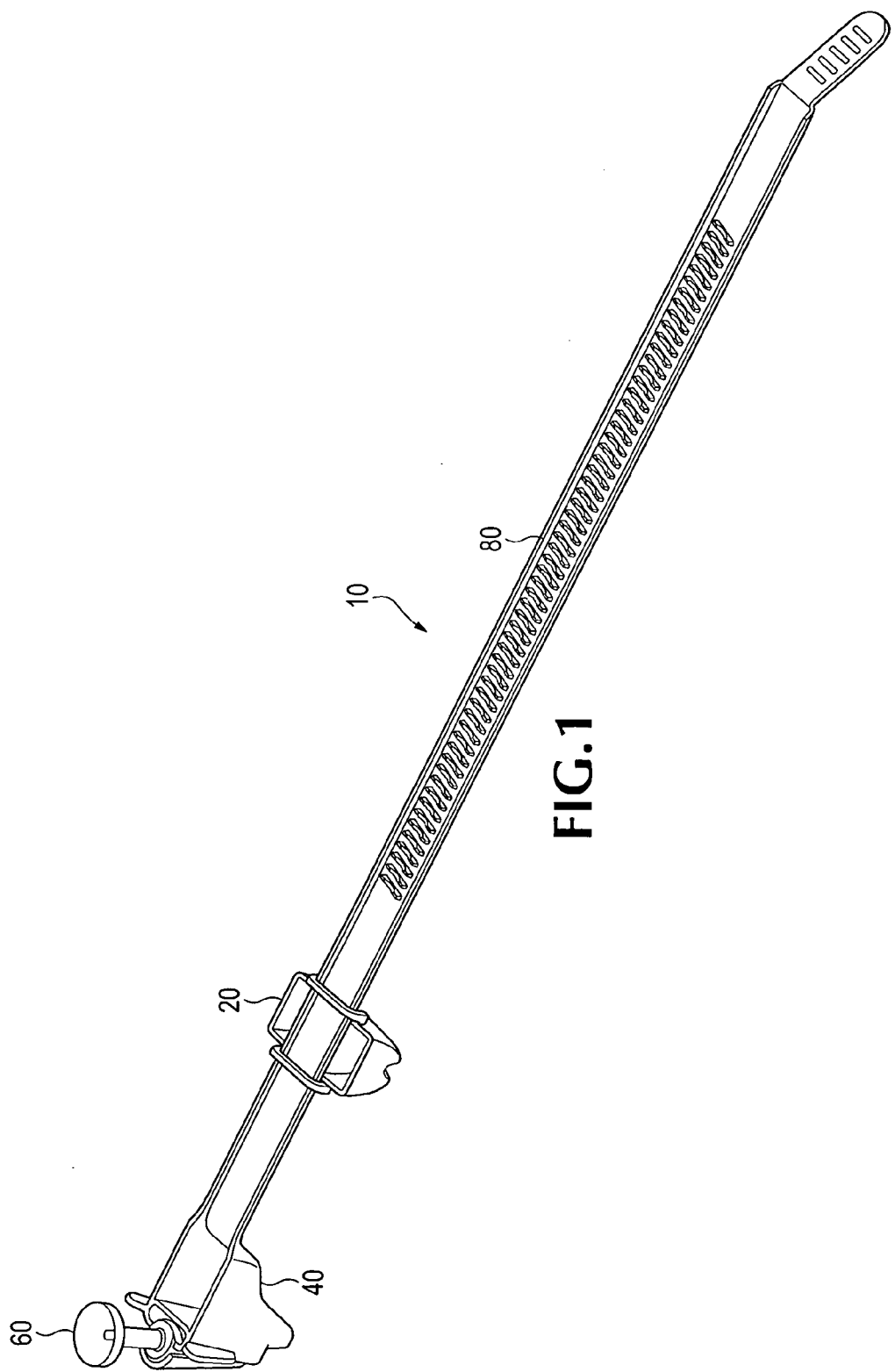

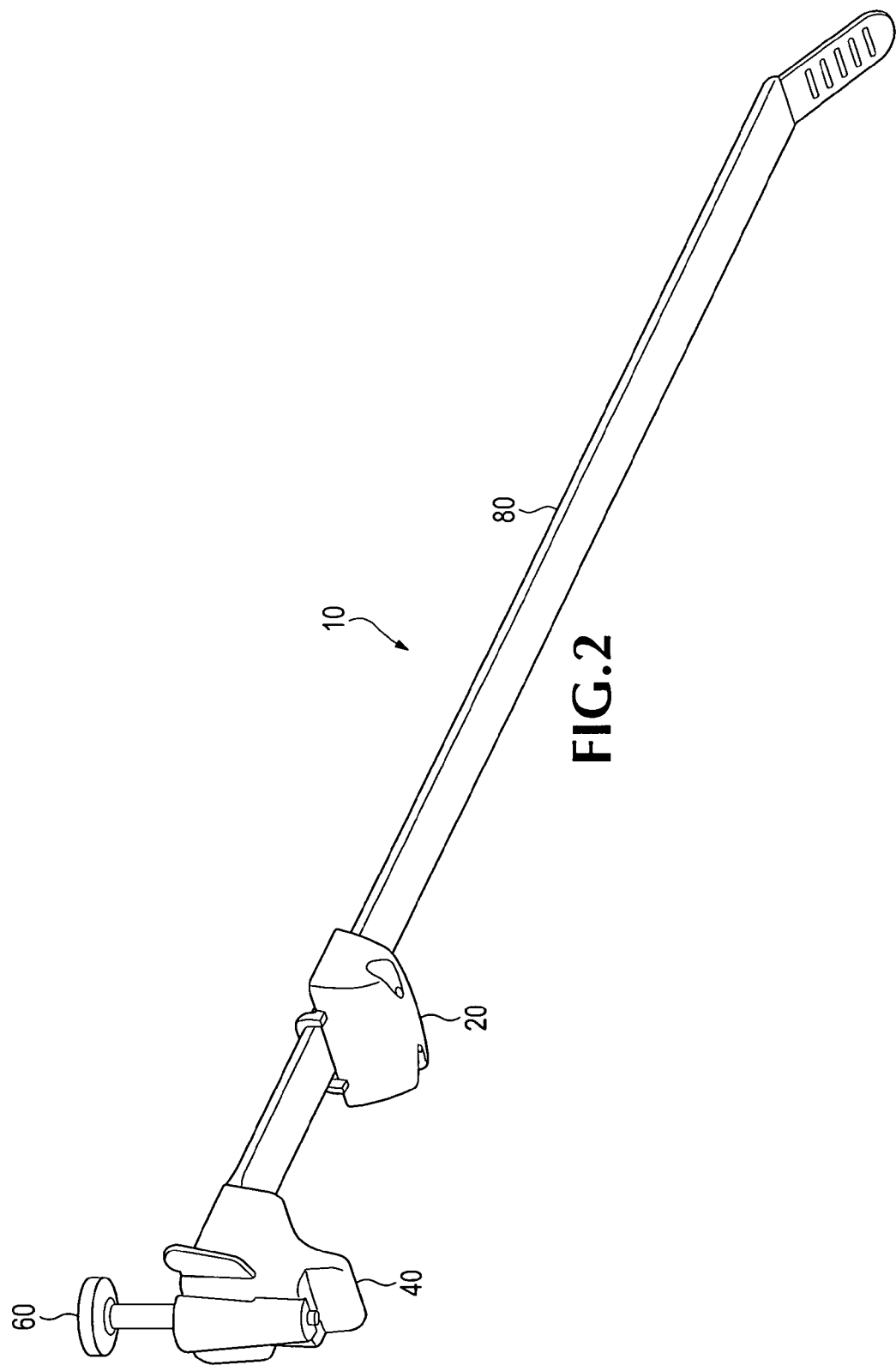

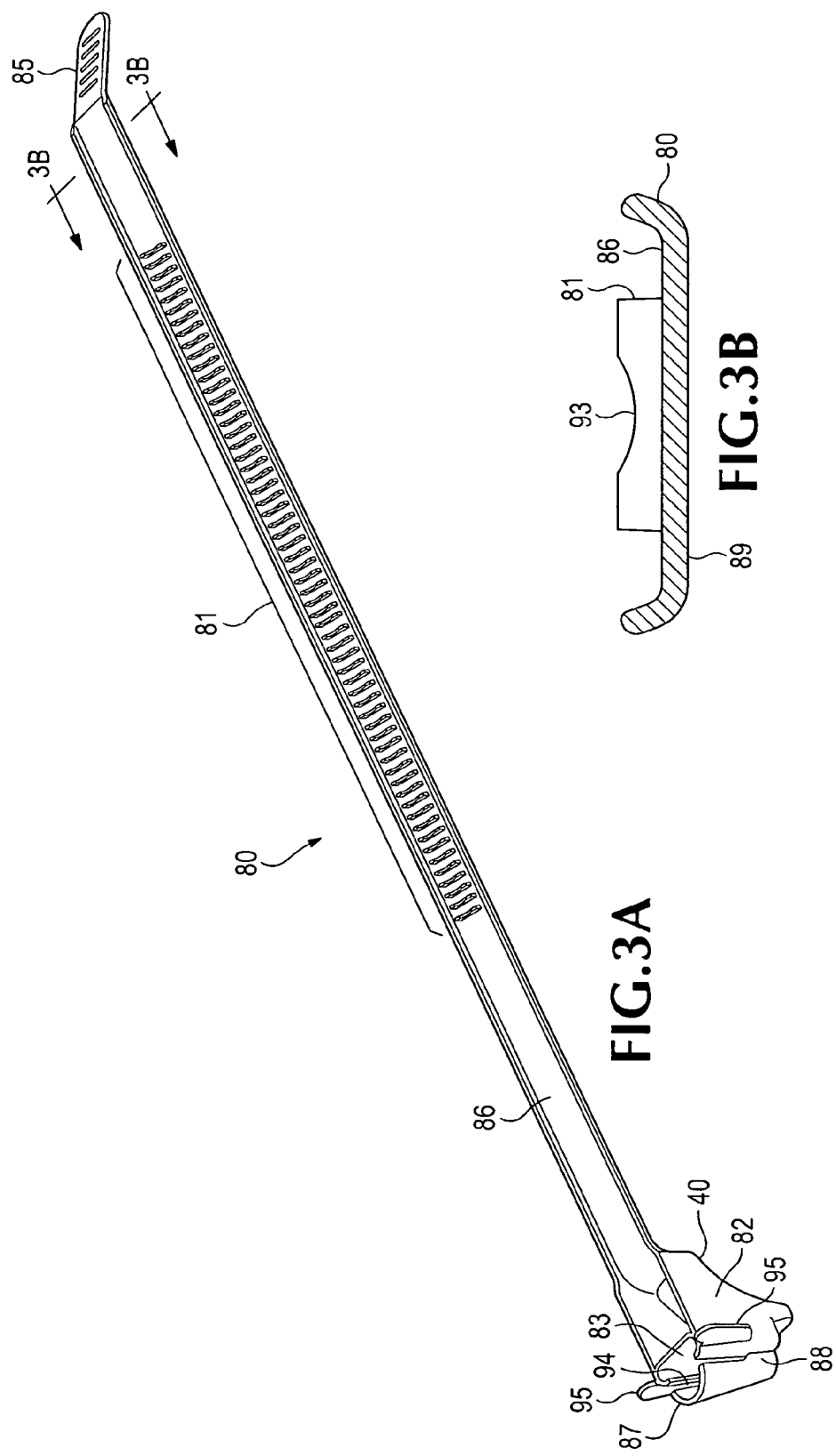

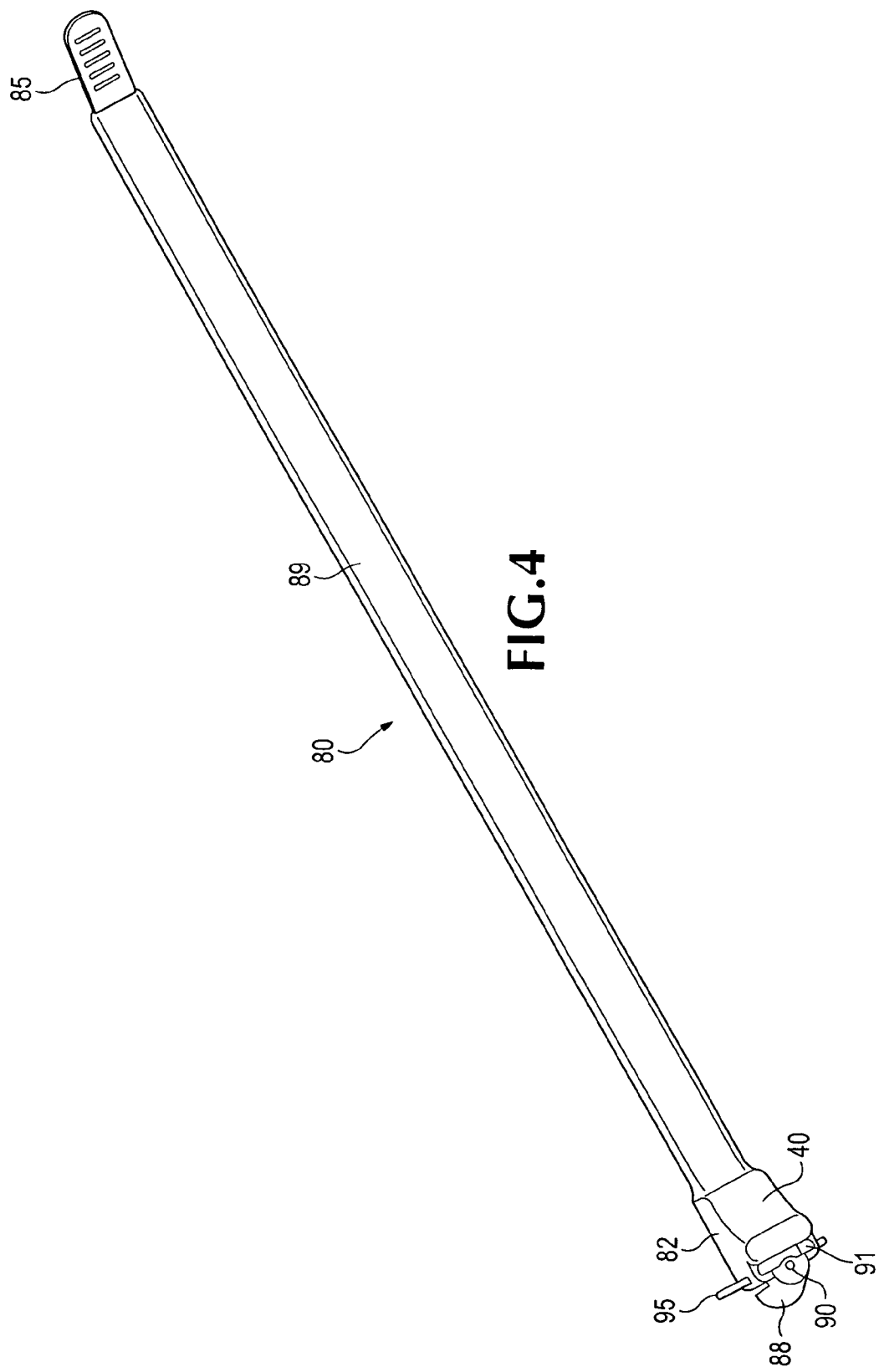

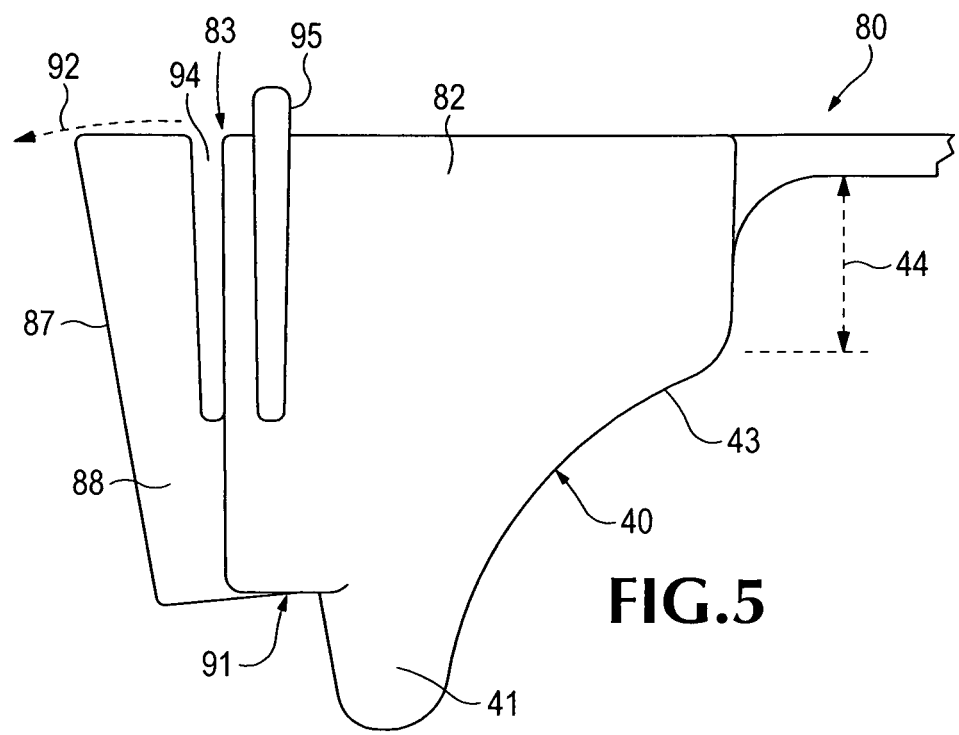
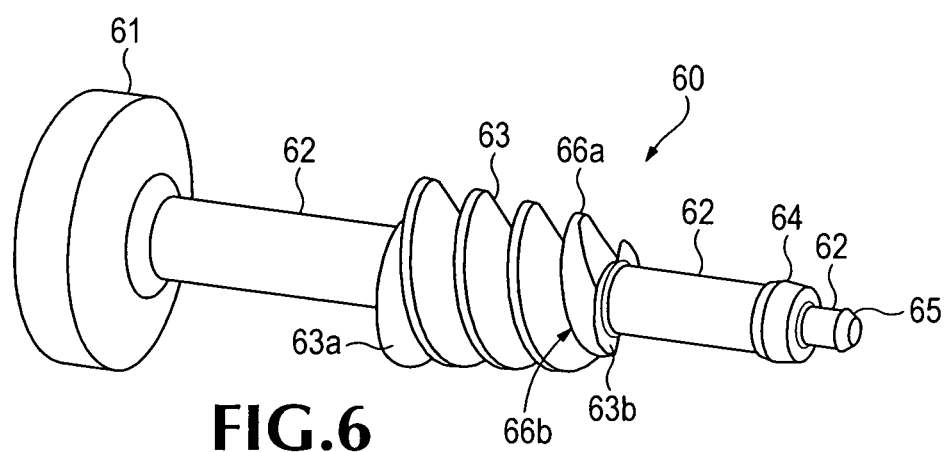

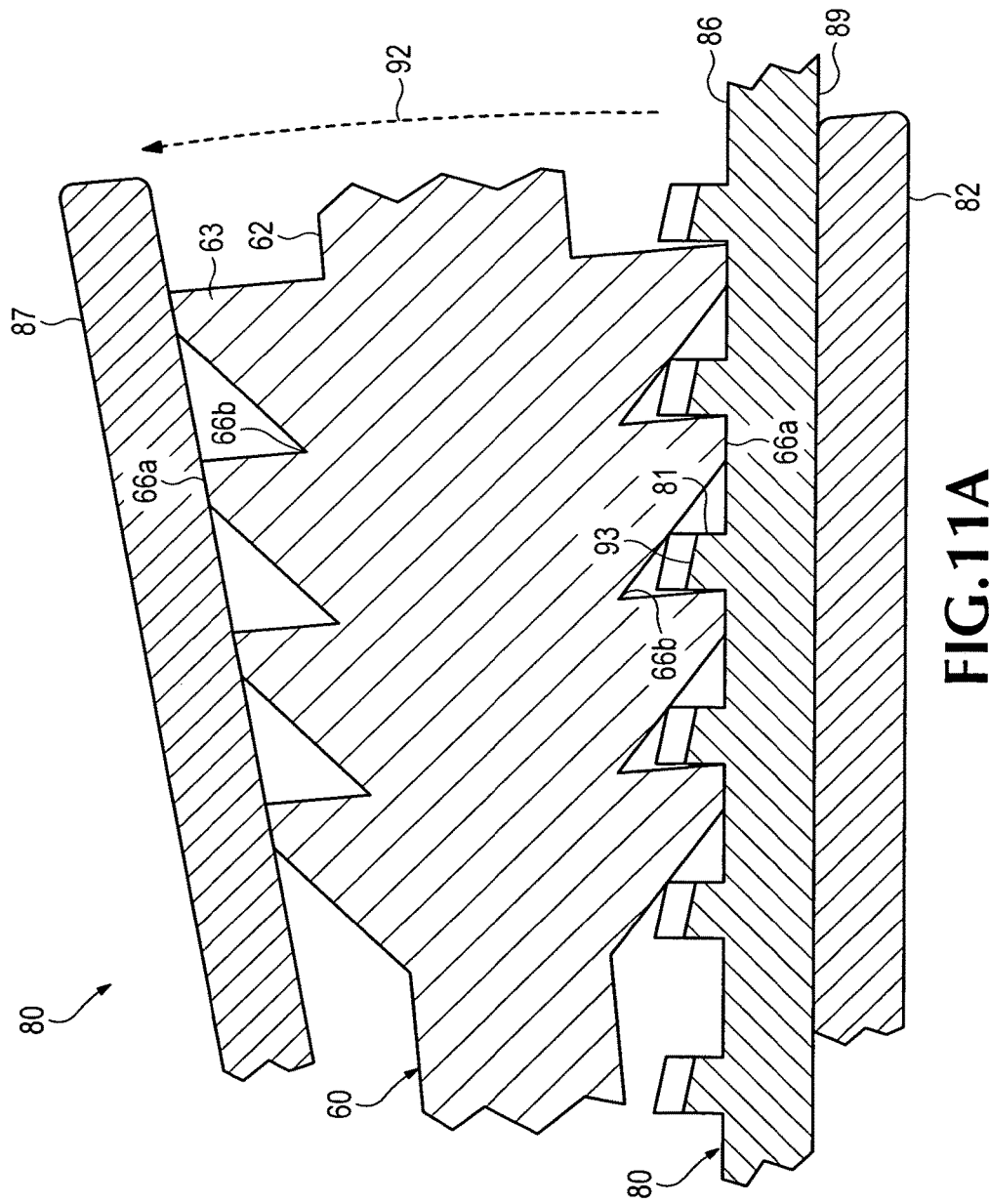

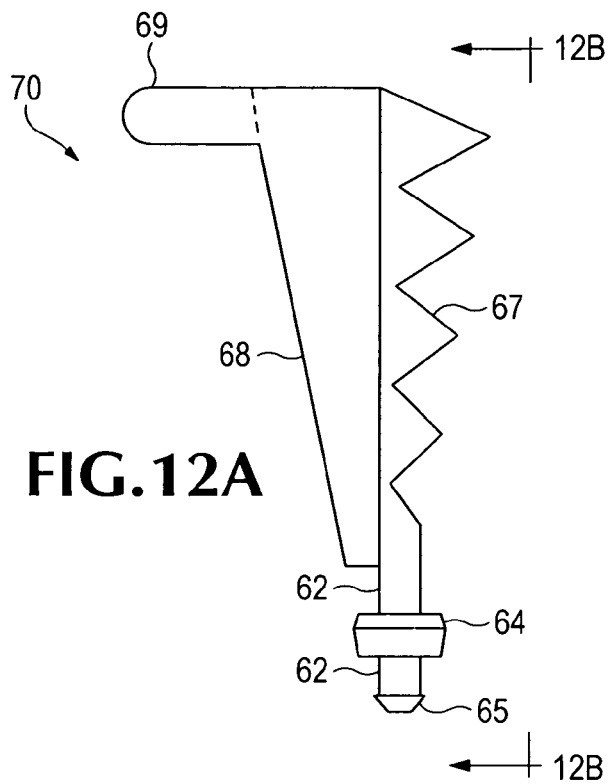
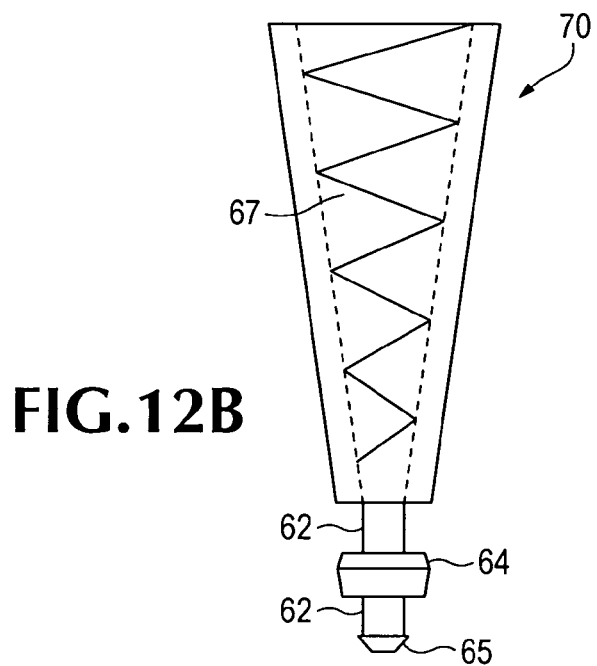

VASCULAR COMPRESSION APPARATUS, PAD AND METHOD OF USE

RELATED APPLICATIONS

This application claims priority to U.S. Provisional Patent Application Ser. No. 61/198,956 filed Nov. 12, 2008, and a 371 of PCT/US09/05892 filed Oct. 30, 2009, the contents of which are incorporated herein in their entirety by this reference.

FIELD OF THE INVENTION

The present invention generally relates to compression devices for occluding blood flow through a blood vessel. More particularly, the invention relates to an apparatus for reducing or stopping blood flow in a blood vessel by means of adjustably applying compression to the body surface overlying said blood vessel.

BACKGROUND OF THE INVENTION

A number of devices have been utilized to externally compress blood vessels in various parts of the body for the purpose of reducing or stopping the flow of blood through said vessels. A tourniquet is a simple device used around a limb which, when tightened, reduces or stops arterial blood flow to the distal portions of the limb and thereby minimizes hemorrhaging from wounds or punctures in the vessels. For medical procedures, tourniquet-type devices have been specifically designed to prevent bleeding through a cannulation or needle puncture in a vessel in a patient's forearm. U.S. Pat. No. 5,269,803 by Geary et al. discloses a strap that encircles the forearm with a pressure pad that applies compression over the vessel to prevent bleeding through the puncture. Other devices that include a strap to prevent bleeding through a puncture site include: U.S. Pat. No. 4,182,338 to Stanulis; U.S. Pat. No. 4,005,709 by Laerdal; U.S. Pat. No. 3,954,109 by Patel; and U.S. Pat. No. 3,586,001 by Sanderson.

Several devices have improved upon the basic tourniquet by applying pressure to only selected points instead of around the entire circumference of the limb, for example: U.S. Pat. No. 6,647,986 by Korotko et al; U.S. Pat. No. 5,728,120 by Shani et al; U.S. Pat. No. 5,601,597 by Arrowood et al; U.S. Pat. No. 5,569,297 by Makower et al; U.S. Pat. No. 5,295,996 by Blair; U.S. Pat. No. 5,234,459 by Lee; U.S. Pat. No. 4,760,846 by Kelly et al; U.S. Pat. No. 4,557,262 by Snow; U.S. Pat. No. 3,570,496 by Sachs; U.S. Pat. No. 2,271,927 by Saighman; and U.S. Pat. No. 1,473,041 by Henderson. Each of these devices includes a strap for encircling a patient's limb, and pressure pads or similar devices to apply compression to stop the blood flow through the target vessels in the limb. A device called the TR Band marketed by Terumo utilizes a wrist-encircling tourniquet-type strap that applies compression by means of an inflatable bladder.

Other devices are known to the inventors, which, although they do not take the form of a tourniquet or derivative device, help achieve hemostasis in blood vessels. Examples include: U.S. Pat. No. 5,304,186 by Semler, et al; U.S. Pat. No. 4,742,825 by Freund et al; U.S. Pat. No. 4,572,182 by Royse; U.S. Pat. No. 4,233,980 by McRae et al; U.S. Pat. No. 3,779,249 by Semler. These disclose mechanical and pneumatic means of applying compression over a blood vessel for the purpose of allowing a clot to form, thereby enabling hemostasis and corollary cessation of bleeding. Features noted in this art are: i) the use of clamping or inflatable bladder mechanisms to apply compression to the body surface overlying a target blood vessel and not all vessels in or leading to the extremity, and ii) the incorporation of features to gradually reduce compression and permit direct visual observation of a surface wound or puncture site leading to the target vessel close to the point of compression.

Additional patents disclose straps that are used in combination with pressure pads for therapeutic purposes other than occluding the flow of blood: U.S. Pat. No. 5,372,575 by Sebastian; U.S. Pat. No. 5,312,350 by Jacobs; U.S. Pat. No. 5,135,473 by Epler et al.; U.S. Pat. No. 5,078,728 by Giarratano; U.S. Pat. No. 4,590,939 by Sakowski; U.S. Pat. No. 4,479,495 by Isaacson; U.S. Pat. No. 4,323,232 by Terpening; U.S. Pat. No. 4,308,861 by Kelly; U.S. Pat. No. 4,243,028 by Puyana; and U.S. Pat. No. 519,894 by Schutz et al.

The prior art teaches that compression applied externally, i.e. on the body surface and over a target blood vessel slows the blood flow such that a clot can form so that normal hemostasis may occur. The prior art further teaches the value of: i) visual and physical access to the puncture or wound site on the body surface, and ii) preferential compression over a target vessel, so that arterial flow to or venous return from an extremity, for example a hand, are important attributes of a device having the purpose of achieving hemostasis following cannulation.

One requirement, well-known to clinical practitioners, which arises following medical procedures involving an arterial puncture, for example, radial artery catheterization, is the necessity to gradually release compression over the vessel to gradually increase blood flow while not disturbing the clot formed during the hemostasis process. Devices used for hemostasis, for example, as described by Semler, provide a means of gradually reducing compression. While there are many references that disclose the broad concept of using a strap with a pressure pad to stop the flow of blood through an arterial puncture wound located on the arm or wrist, none of these devices provides a convenient, user-controlled, easily-adjustable means of: i) rapidly applying compression to a blood vessel while the cannula is removed, and ii) adjusting the amount of compression being applied to the point of compression in fine increments without releasing the fastening mechanism of the apparatus, and iii) quickly releasing compression and removing the device from the patient, and iv) integrating the adjustment and fastening means to enhance ease of use, and v) enabling distal blood flow through adjacent blood vessels, for example, distal blood flow through the ulnar artery and venous return from the hand. Therefore, a need exists for an adjustable vascular compression device.

SUMMARY OF THE INVENTION

The present invention generally relates to devices for use following cannulation procedures performed on blood vessels in a limb of a patient, for example, during or after radial artery catheterization procedures, or during or after a hemodialysis session, or during or after withdrawal of a cannula from a vein or artery in a patient's arm. More particularly, the present invention describes an adjustable vascular compression device which applies compression on a patient's body surface overlying a blood vessel thereby constricting said vessel, for the purpose of reducing or stopping blood flow at that point of compression, for example, proximal to or over a radial artery puncture site, to permit hemostasis to occur at the site by reducing or eliminating blood flow at and distal to the point of compression. Alternatively the compression may be applied directly over the puncture site or at a point distal to the puncture site. Thus, the present invention provides utility in assisting with hemostasis following medical cannulation procedures on the limbs of a patient, for example, in: radial artery catheterization procedures for interventional cardiology, diagnostic cardiology and radiology; surgery; other cardiac procedures including electrophysiology; kidney dialysis; and, withdrawal of catheters, wires or other cannulae from a patient's blood vessels for other medical applications.

The compression device of the present invention has, features that permit sufficient adjustable compression to be applied to a target blood vessel in a patient's limb, for example, a radial artery, while, at the discretion of the user deploying the device on a patient, also maintaining blood flow through the target vessel or other vessels in the limb. For example, the device may be used to partially or fully occlude blood flow through a radial artery, with adjustments by the user to gradually increase flow as hemostasis occurs, while simultaneously permitting distal arterial blood flow through the ulnar artery and venous return from the hand. In addition, the device further provides: i) a securement means for quickly fastening the device around the patient's wrist and providing compression over the artery, ii) an adjustment means for the user to adjust the compression in small increments and iii) a release means further enabling rapid release of compression and removal from the wrist. More particularly, the device may be quickly secured and tightened as a cannula is removed to provide compression over the cannulated artery, and subsequently such compression may be tightened or loosened in small continuous increments at the user's discretion without releasing the primary means by which the device is secured.

Preferably, the apparatus is formed of materials that may be assembled, packaged and pre-sterilized for single-use applications. Alternatively, the device may be provided in partially assembled or non-sterilized form.

In view of the above, an object of the adjustable vascular compression device of the present invention is to provide an apparatus that provides external compression, i.e. onto a body surface, which in turn compresses an underlying target blood vessel for the purpose of slowing or stopping blood flow to assist in achieving hemostasis of a puncture or wound.

Another object of the present invention is to enable the device to be rapidly applied and fastened to the patient and, following use, rapidly removed from the patient.

Another object of the present invention is to enable a user operating the device to make fine adjustments in the amount of external compression applied to the vessel following device deployment without releasing the fastening mechanism, one purpose of which is to enable adjustment to permit user-controlled "patency" of the vessel (i.e. the extent of flow therethrough) during compression.

Another object of the present invention is to provide a user with both visual and physical access to the area of the puncture site while the compression device is applied to the patient.

Another more particular object of the present invention is to provide external compression of a target blood vessel, specifically an artery or vein in the arm or wrist, directly over or near to a puncture site on the body surface, which leads to an arteriotomy or venotomy, for the purpose of stopping or slowing distal blood flow.

Another more particular object of the present invention is to provide user-adjustable external compression of a radial artery, following a catheterization or other medical cannulation procedure, such that the vessel under compression retains a degree of patency.

Another more particular object of the present invention is to provide external compression of a target blood vessel while permitting generally unimpeded flow of blood in other adjacent blood vessels, for example, limiting or stopping blood flow in the radial artery while permitting distal flow through the ulnar artery to the hand and venous return from the hand.

The device of the present invention achieves these and other objects through its inclusion of elements that generally include a strap having threads at one end and a housing at the other end, a compression pad, and a threaded element. The device may further include an ulnar pad. Though these elements are described and shown as separate elements assembled into a single device it will be understood that they may alternatively be composed as an assembly having fewer or more separate elements, for example, one or both of the radial and ulnar pads may be formed with the strap as a single unitary element.

A housing located at one end of the strap holds the threaded element, more particularly, a fully rotatable adjustment screw, within it and further provides sufficient flexion, through a hinge means at one end, to enable quick release of the strap when the hinge means is flexed. Pulling on the screw contained within the housing perpendicularly to its longitudinal axis would then cause it to act as a lever, and is a means of effecting such flexion of the hinge means. As an alternative to using a fully rotatable adjustment screw, a fully or partially threaded bolt which is non-rotatable or which has a maximum rotation of less than 360 degrees, more particularly less than 240 degrees, may be included as the threaded element. A threaded element may also be integrally formed as a non-separable, for example, molded in, part of the strap.

The end of the strap opposite the end on which the housing is located is passed through the housing so that the strap encircles the arm or wrist of the patient. Threads on the strap which engage the threaded element provide a securement means for fastening the device around the arm or wrist of the patient. The fit of the threaded element within the housing and the engagement of its threads with the threads of the strap enables the strap to be quickly tightened and retained under tension around the arm or wrist, and permits easy movement of the strap through the housing when the strap is being pulled through. When an adjustment screw is used, by rotating it, tension is gradually increased or decreased as the threads on the screw engage the threads on the strap to change the circumference of the strap around the arm or wrist, thus enabling the gradual fine adjustments without releasing the fastening mechanism. Thus, in combination with the housing through which the strap is passed, the adjustment screw and the threads on the strap further provide an adjustment means. Pulling the screw away from the strap and perpendicularly to its longitudinal axis would then cause it to act as a lever to flex open the hinge means, thereby decoupling the threads on the strap from the threads on the threaded element, providing a release means. The apparatus thus enables both rapid securement and release, and fine adjustments to tension without releasing the means of securement.

In the event that a fully or partially threaded bolt is employed, said bolt may be fit in place of the rotatable adjustment screw into the housing, to simply engage with the threads on the strap to provide the securement means, without the ability to make fine tension adjustments. The threads of the bolt are present on at least the side facing the threads on the strap when the strap is inserted into the housing. A tab, handle or other grasping means on either an exposed portion of the threaded element or on the housing provides a lever to enable the user to deflect the housing in its vertical axis, to provide the release means, to permit quick release of the strap.

The compression pad provides preferential compression directly over the radial artery. The ulnar pad provides a cushion against the ulnar side of the forearm. The ulnar and compression pads also position the strap away from the body surface of the forearm to enable blood flow through underlying blood vessels. One or both of the pads may be integrally formed as non-separable, for example, molded-in, parts of the strap, or may be formed as separate parts to be attached to the strap. The pads may be formed in a variety of shapes, each suitable for a specific application, for example, a pad having a notch or holding means for an absorbent or other material, for example having hemostatic properties, may be employed for hemostasis of hemodialysis needle sites while a pad having an elongate shape may be employed for a post-catheterization hemostasis of a radial artery. Such pads can further include additional materials attached to their surfaces that make contact with a patient's body surface for the purpose of providing cushioning, for comfort, or for assisting with the compression of the target blood vessel, or for otherwise assisting with the medication or hemostasis of the puncture site in the blood vessel. A notch or groove may be further included on the bottom of such pad to guide placement of the pad over the cannula inserted into the puncture site on the skin surface, to provide accurate placement of compression.

All or part of the apparatus, including the compression pad, may also be composed of a material having anti-microbial properties sufficient to prevent growth of microbes or to kill microbes with which it comes into contact, for example on the skin of a patient on whom the apparatus is deployed. Alternatively, the exterior surfaces of the compression pad or other components of the apparatus may be treated with a process or material having anti-microbial properties. Examples of these processes and materials, which are well-known to those skilled in the art, can include: i) the deposition of silver or organic or inorganic particles onto the surfaces of the components of the apparatus by means of vapor deposition or liquid immersion; or ii) including silver or organic or inorganic particles mixed into the materials from which the components are formed.

It will be understood by those skilled in the art that, although the following drawings and Detailed Description disclose further aspects and advantages of the apparatus and describes preferred embodiments, the present invention is not intended to be limited only to these preferred embodiments. It will be apparent that other changes in form and detail may be made therein without departing from the spirit and scope of the invention as defined in the appended claims.

BRIEF DESCRIPTION OF THE DRAWINGS

FIG. 1 is a top isometric view of an adjustable vascular compression device.

FIG. 2 is a bottom isometric view of the device.

FIG. 3A is a top isometric view of a strap element of the device.

FIG. 3B is an end view of a strap thread element of the strap element, taken along lines 3B-3B of FIG. 3A.

FIG. 4 is a bottom isometric view of the strap element.

FIG. 5 is a side elevation of a housing of the strap element.

FIG. 6 is a side isometric view of a screw element of the device.

FIG. 11A is a fragmentary, cross-sectional elevation, with parts removed, of screw threads engaging the strap threads on a notch of the strap threads inside the spring guide of housing of the strap element.

FIG. 12A is a side view of a bolt.

FIG. 12B is a bottom view of the bolt taken along lines 12B-12B of FIG. 12A.

DETAILED DESCRIPTION OF THE PREFERRED EMBODIMENTS

Figure 7A:
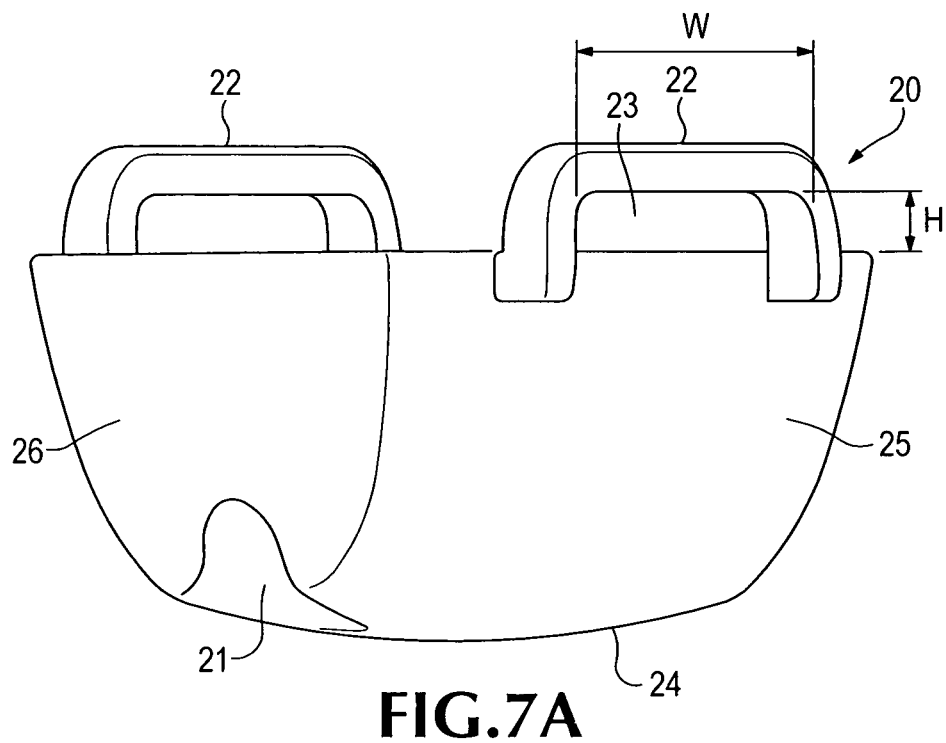
FIG. 7A is a side isometric view of a compression pad element of the device.

An adjustable vascular compression device 10, for use in assisting with post-procedure radial artery hemostasis following catheterization or other cannulation, is shown in the drawings and Detailed Description included herein as a preferred embodiment of the present invention. Although parts are described as discrete components and features are described with specific structures, it will be understood by those skilled in the art that alternative means of construction to achieve the same purpose may be employed without deviating from the present invention.

As illustrated, FIGS. 1 and 2 show an adjustable vascular compression device 10, which includes a strap 80 to which a threaded element, more particularly a compression pad 20 and an adjustment screw 60 are attached. (Those of skill in the art will appreciate that a bolt or other fixation device, e.g. a bolt 70, may be used as an alternative to an adjustment screw 60, as indicated in FIGS. 12A and 12B. Other suitable alternatives for a threaded element are contemplated as being within the spirit and scope of the invention.) Strap 80 is configured to be slidably received through openings provided in a compression pad to be described below, and strap 80 is dimensioned to have a width W of between approximately 0.2 centimeters and approximately 5.0 centimeters, more particularly between approximately 0.5 and approximately 2.5 centimeters to correspond nominally and substantially with the dimensions of such openings, as described and illustrated herein.

FIG. 3A further shows that the strap 80 includes at one end an angled strap tip 85 and at the opposite end a housing 82, one side of which comprises the ulnar pad 40. The housing 82 further includes a spring guide 87 (alternatively referred to herein as a release lever), a spring hinge 88, a cutout 94 and a strap-tip exit opening 83. Strap threads 81 are shown on a top surface 86 of strap 80. The width W (refer briefly to FIG. 7A) of the strap 80 may be between 0.2 centimeters and 5 centimeters, more particularly between 0.5 and 2 centimeters. The height H (refer briefly to FIG. 7A) of the strap 80 may be between 0.2 millimeters and 10 millimeters, more particularly between 0.5 millimeters and 5 millimeters. Fingertip tabs 95 are shown on either side of the housing 82.

Tabs 95 will be appreciated by those of skill in the art to leverage the release of spring hinge 88. The tabs can be used singly or collectively with one or more fingers of either user hand to oppose the thumb's arcuate or pivotal movement of spring guide 87 outwardly away from the body of housing 82, thereby to facilitate release strap 80 from housing 82. Alternative configurations of one or more tabs or wings on housing 82 are contemplated as being within the spirit and scope of the invention.

FIG. 3B shows a strap thread 81 in end view taken along lines 3B-3B of FIG. 3A. A bottom surface 89 of the strap is shown as is a concave notch 93 in the center of an upper region of the thread 81 opposite the bottom surface 89.

FIG. 4 further shows a strap-tip insertion opening 91 and screw retention hole 90 located near the spring hinge 88 on the housing 82. Insertion opening 91 will be understood to accept angled end 85 of strap 80 to be inserted thereinto as the strap is placed around a wrist.

Figure 9:
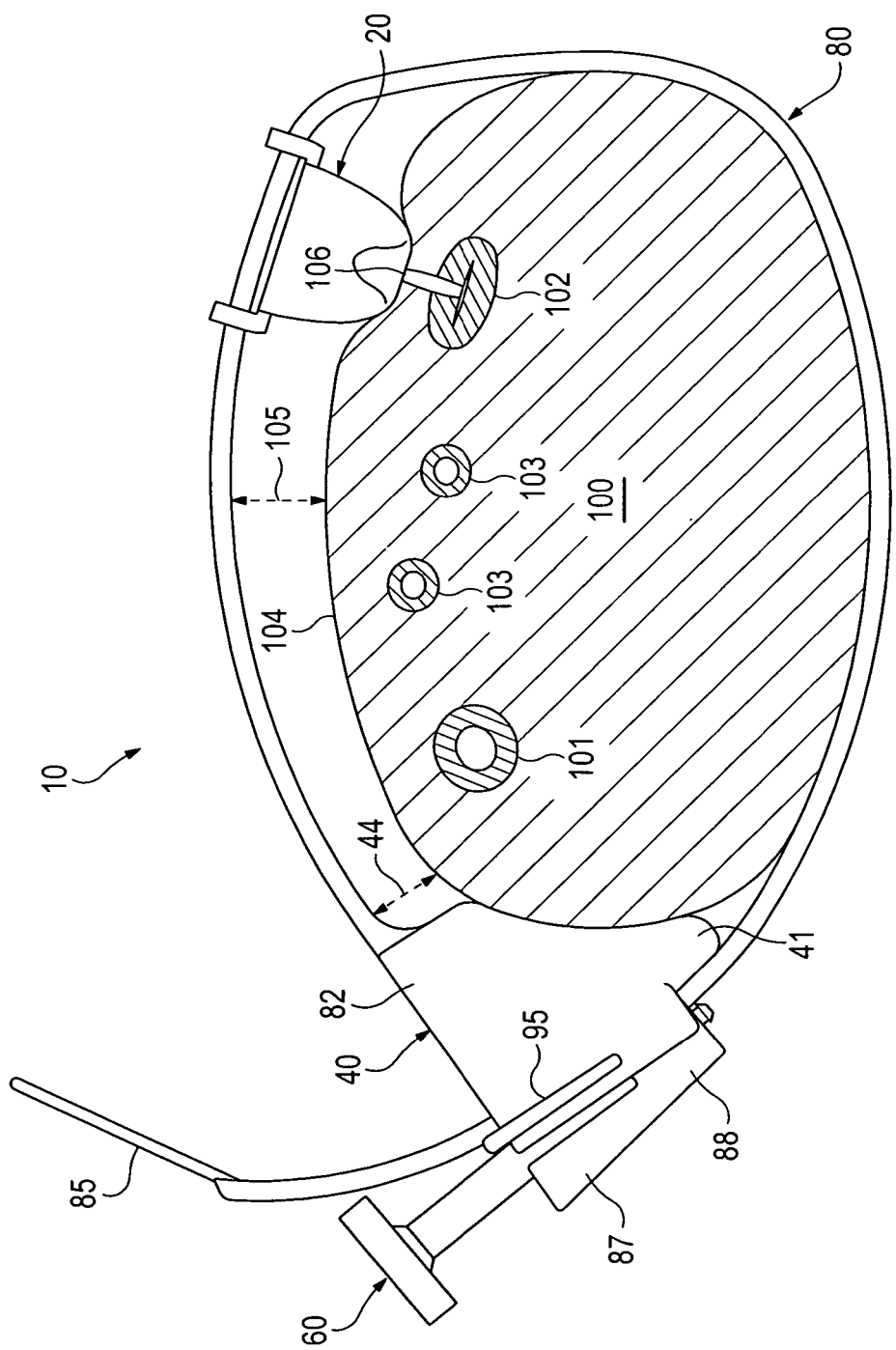
FIG. 9 is a cross-sectional view of a wrist, with the apparatus attached.

FIG. 5 shows additional elements of the housing 82, including the ulnar pad 40, the tail 41 of the ulnar pad, convex surfaces 43 of the ulnar pad and its height 44, which creates a wrist-standoff space 105 shown in FIG. 9. FIG. 5 further shows the exit opening 83, the insertion opening 91, a cutout 94 that creates the spring hinge 88, and an arc or arcuate axis 92 that represents the direction of movement of the spring guide 87 permitted by the spring hinge 88.

FIG. 6 shows the elements of the adjustment screw 60 including a generally frusto-conical or tapered shaft 62, threads 63 having a top end 63a and bottom end 63b, a stop ring 64 and retention knob 65. The screw threads 63 have outside helical edges 66a and corresponding inside helical edges 66b. The stop ring 64 and retention knob 65 serve to retain the screw 60 in the screw insertion hole 90 and spring guide 87. The screw 60, when retained in place in the spring guide 87 and with its screw threads 63 meshing with the strap threads 81, serves as both a fastening and compression adjustment means for the device 10.

Figure 7B:
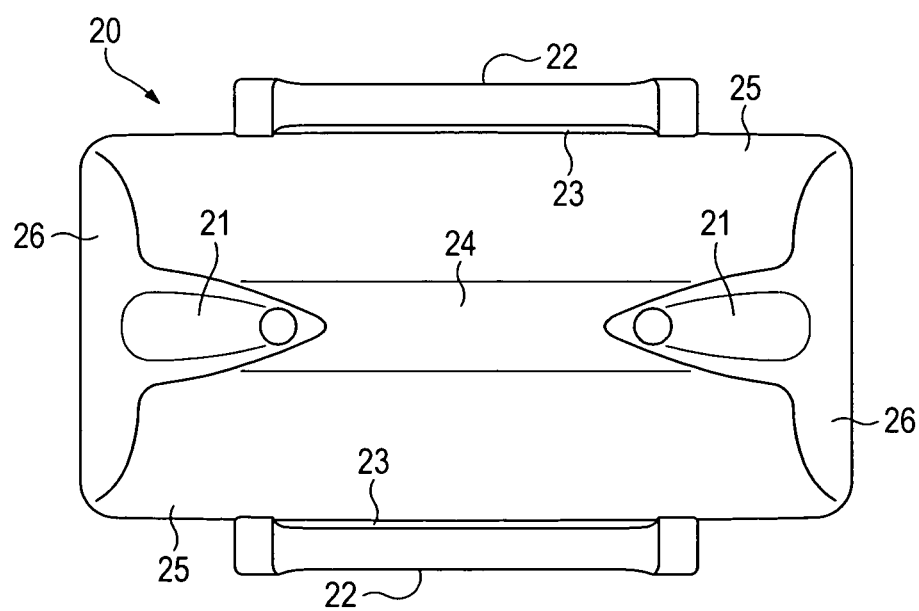
FIG. 7B is a bottom view of the compression pad element.
Figure 10A:
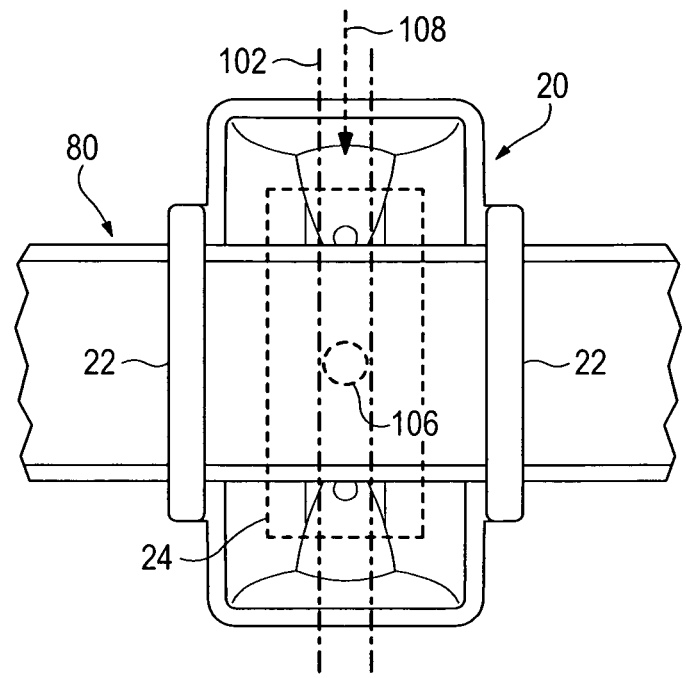
FIG. 10A is a fragmentary plan view of the apparatus attached to a wrist, with parts removed for clarity.

FIGS. 7A and 7B show side and bottom aspects of the compression pad 20, designed for placement directly over a puncture site 106 as shown in FIG. 10A. Loops 22 create strap openings 23 through which strap-tip 85 and an adjustable length of the strap 80 passes. In accordance with one embodiment of the invention, the strap openings are configured to fit slidably around the strap, and are dimensioned to have a width W of between approximately 0.2 centimeters and approximately 5.0 centimeters, more particularly between approximately 0.5 and approximately 2.5 centimeters. Also in accordance with one embodiment of the invention, the strap openings have a height H of between approximately 0.2 millimeters and approximately 10 millimeters, more particularly between approximately 0.5 millimeters and 5 millimeters. Those of skill in the art will appreciate that these nominal measurements H and W of the openings are applicable also to the respective height and width of strap 82 which is received therethrough. Alternative opening widths and heights are contemplated as being within the spirit and scope of the invention.

The body of the compression pad 20 comprise end sidewalls 26, lateral sidewalls 25 and a compression surface 24 on the bottom. A notch 21 is located on the compression surface 24, which may be located at one end or on each end of the pad 20. The notch 21 serves to help the user position the pad 20 during deployment onto a patient and further provides a path for a cannula when it is withdrawn from the blood vessel. The strap openings 23 are of a size such that the strap loops 22 fit over the strap 80, such fit enabling slidable movement of the compression pad 20 along the length of the strap 80 and adjustment for such variables as wrist circumference, desired vascular compression, and patient comfort.

In accordance with one embodiment of the invention, the compression pad 20 is dimensioned as follows: The footprint of the pad has an area of between 1.0 and 5.0 square centimeters, or more particularly a length of approximately 2.95 centimeters and a width of approximately 0.9 centimeters for a nominal 2.66 $cm^2$ patient skin contact surface area. The nominal height of the pad 20 that determines the nominal height of space 105 is approximately 0.5 centimeters, although it will be appreciated that any suitable height between approximately 0.25 to 5.0 centimeters is contemplated as being within the spirit and scope of the invention. All dimensions are approximate due to rounded edges and corners. Moreover, those of skill in the art will appreciate that alternative dimensions are contemplated as being within the spirit and scope of the invention. Those of skill in the art also will appreciate that alternative configurations, shapes, contours, and radii of curvature are contemplated as being within the spirit and scope of the invention.

Those of skill in the art will appreciate that compression surface 24 can be rigid or yieldable, i.e. somewhat compressible or malleable. For example, it can be formed to have a lower, skin contacting surface that 'gives' slightly when pressed against a person's skin, or it can be covered by a material that is so characterized, thereby further increasing the comfort to the patient during use of the invented apparatus. Such compression surface 24 may be formed as a unitary part of the compression pad 20, or alternatively as a separate element, e.g. a material expanse, that is attached to the compression pad 20.

Figure 8A:
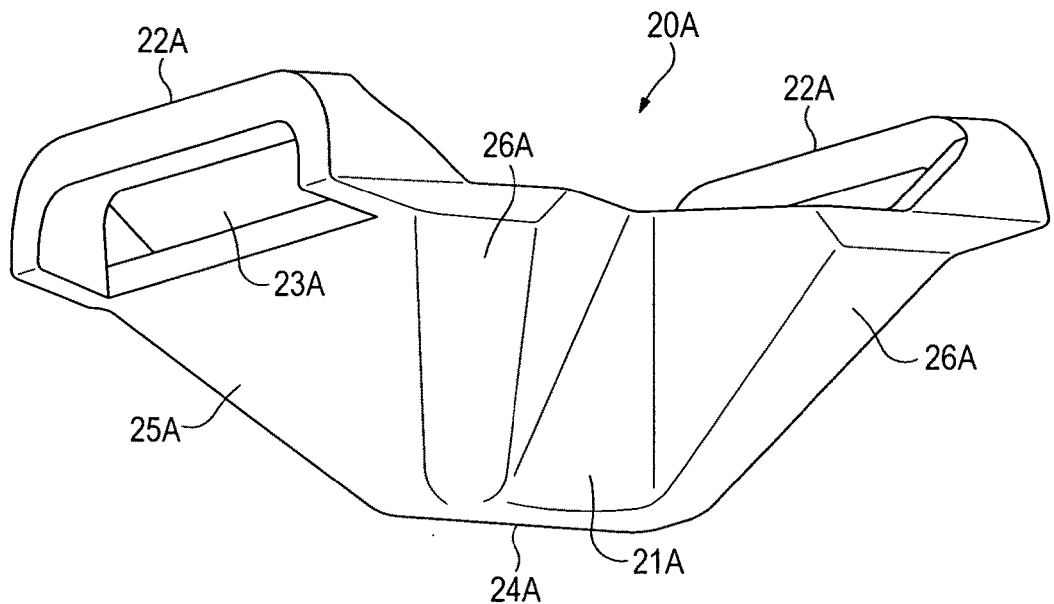
FIG. 8A is a side isometric view of an alternative embodiment of the compression pad element.
Figure 10B:
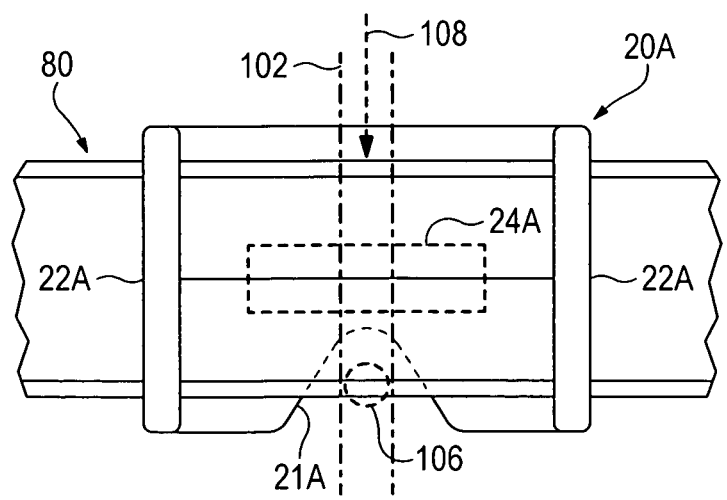
FIG. 10B is a fragmentary plan view of an alternative embodiment of the apparatus attached to a wrist, with parts removed for clarity.

FIG. 8A shows an alternative embodiment of a compression pad 20A, which includes elements similar to the preferred embodiment of the compression pad 20, but positioned in a different configuration for use proximal to a puncture site 106 shown in FIG. 10B. Loops 22A, strap openings 23A, compression surface 24A, lateral sidewalls 25A and end sidewalls 26A are shown in compression pad 20A as alternative embodiment features analogous to loops 22, strap openings 23, compression surface 24, lateral sidewalls 25 and end sidewalls 26 of the compression pad 20 to which their reference designators correspond. Those of skill in the art will appreciate that the more angular facial (faceted) features of this embodiment of compression pad 20A provides a larger and deeper notch 21A providing a larger and deeper cannular approach, e.g. a slightly larger target zone, for visual and physical access to the radial artery or other blood vessel. This alternative embodiment of the pad might be used for example for hemodialysis, but not for radial artery cannula removal. With the radial artery, given its proximity to the palmar arch which is an artery that connects the radial artery and the ulnar artery, pad placement proximal to the access site may not work since the ulnar artery blood flow may cause bleeding from the site. With a shunt, pad placement proximal to the site may work since the ulnar blood flow does not necessarily create the 'backflow' to cause bleeding from the puncture site. FIG. 8A shows a pad designed for proximal placement, with the notch 21A providing both visual and fingertip access to the puncture site.

In contrast, with the compression pad of FIG. 7A, the rounded feature avoids sharp edges which could create patient discomfort when the device is applied under compression. It also provides more skin surface coverage as compression increases since the pad will "sink" into the tissue, since muscle and fat tissue is generally compliant. The notch 21 enables better positioning of the pad along the longitudinal axis of the target blood vessel, i.e. the radial artery, since the cannula protruding from the puncture site will fit over the notch 21, thus guiding the user to properly place the pad directly over the puncture site and not proximal or distal, or off to one side. The slightly convex shape of the bottom surface 24 also helps make deployment more comfortable for the patient by avoiding hard edges of the pad. It further focuses compression at the center point of the surface 24 as well as providing a long surface for compressing (albeit at a slightly lesser amount) the target vessel proximal and distal to the arteriotomy. This provides some small placement error margin, which may be needed since the arteriotomy, though close to the puncture site, is not directly under it.

Figure 8B:
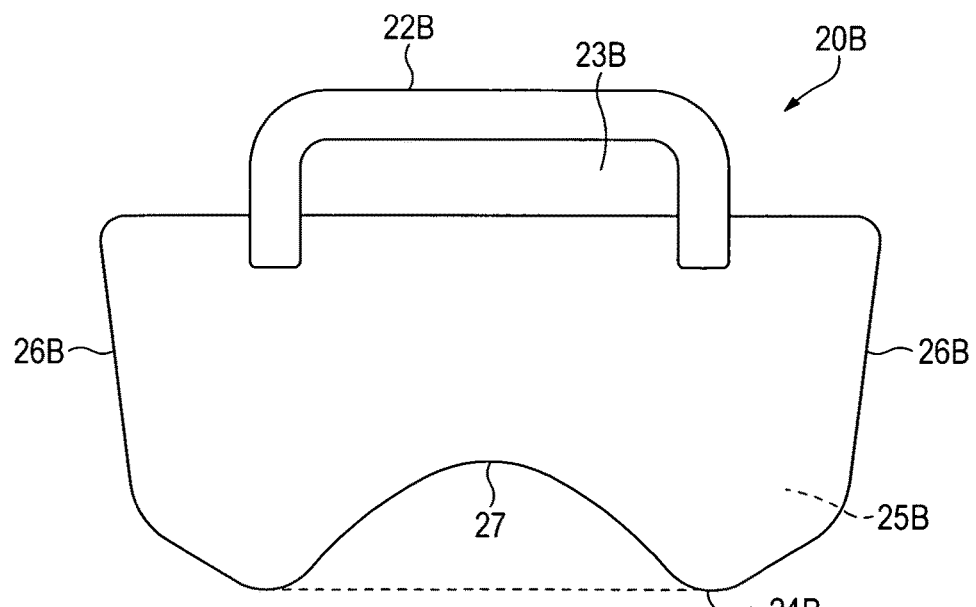
FIG. 8B is a side elevation of an alternative embodiment of the compression pad element.

FIG. 8B shows an alternative embodiment of a compression pad 20B which includes elements similar to the preferred embodiment of the compression pad 20, for use over a puncture site 106 as shown in FIG. 10A. Included are loops 22B creating strap openings 23B, lateral sidewalls 25B, end sidewalls 26B, a compression surface 24B, and further including a concavity 27 located in the compression surface 24B for enabling physical and visual access to the puncture site 106. Alternatively, the concavity 27 can be used to attach a separate component to the compression pad 20B. For example, a piece of medical gauze, a sponge, a pad, a hemostatic material, or another object can be removably attached in concavity 27 to assist in compressing the puncture site 106. The concavity 27 can assume alternative forms including a trough-like concavity extending from side to side, or a pocket or depression generally within a central lower surface of the compression pad 20B, having sidewalls all around (as suggested by the horizontal dashed line along the bottom surface of the pad in FIG. 8B). The concavity can be of a regular shape, e.g. a trough of generally semicircular or parabolic cross section as shown or a pocket of generally semispherical or other regular geometric cross section. Alternatively, the concavity can be of an irregular shape to accommodate any object of irregular shape therein.

FIG. 9 shows application of the device 10 onto a wrist 100 for the purpose of occluding a blood vessel 102, in this case a radial artery, while keeping the ulnar artery 101 and veins 103 "patent" (relatively open to blood flow), by means of the standoff space 105 created between the strap 80 and the surface of the wrist 104.

FIG. 10A shows the preferred embodiment of the compression pad 20 in position directly over the blood vessel 102 and puncture site 106, with its compression surface 24 overlying the blood vessel 102 in its longitudinal axis.

FIG. 10B shows an alternative embodiment of the compression pad 20A in a position proximal to the puncture site 106 and over blood vessel 102. The compression surface 24A lies over the blood vessel 102 but exposes the puncture site 106 by means of the notch 21A.

Figure 11B:
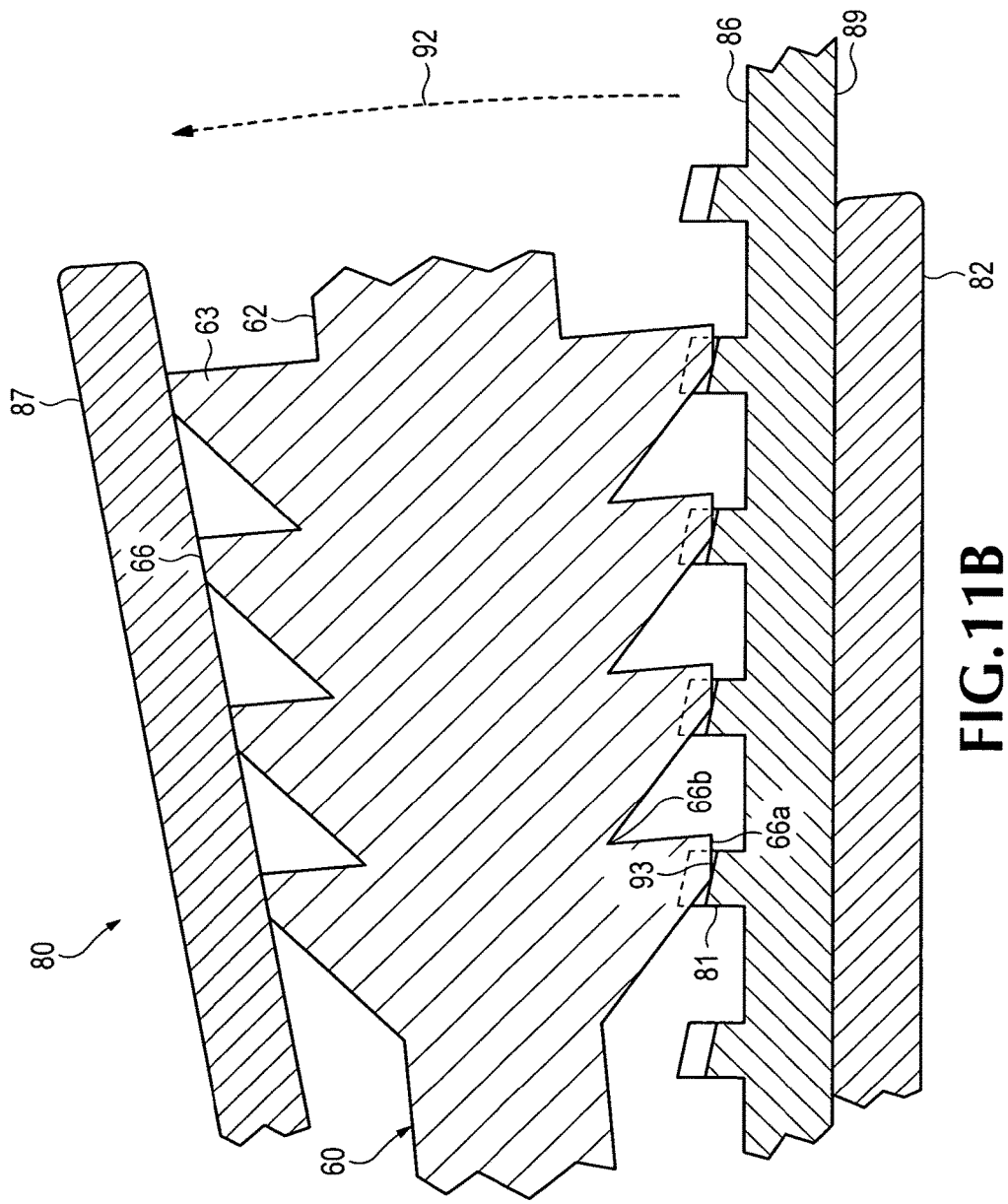
FIG. 11B is a fragmentary, cross-sectional elevation, with parts removed, of screw threads engaging the strap threads off of the notch of the strap threads inside the spring guide of housing of the strap element.

FIGS. 11A and 11B show the screw 60 in place in the spring guide 87 of the housing 82, the strap threads 81 engaging with the screw threads 63. FIG. 11A shows the outside edges 66a of the screw threads in full contact with both the interior surface of the spring guide 87 and the portions of the top surface 86 of the strap 80 located between the threads 81. In this position, the strap 80 is retained in place against a pulling force of a user attempting to unfasten the device, since the screw threads 63 block movement of the strap threads 81. FIG. 11B shows the screw 60 and its screw threads 66 elevated onto the concave notch 93 of the strap threads 81 when the strap-tip 85 of strap 80 is pulled to fasten the device. The movement of the strap 80 in the fastening direction causes the screw threads 63 to move to engage the concave notch 93 and travel up on top of them, this movement of the screw 60 in the vertical axis 92 being permitted by the opening of the flexible spring hinge 88 (not shown in these figures) as it is forced open by the vertical travel of the screw 60. Thus when being fastened, the strap 80 is able to move in the fastening direction, but not in the unfastening direction due to the meshing of the screw threads 63 and strap threads 81. As the strap 80 continues to move in the fastening direction the concave notches 93 on the strap threads 81 move out from underneath the screw threads 63, enabling the screw 60 to move downwards in the arcuate axis 92, this movement being caused by the closing of the spring hinge 88.

FIGS. 12A and 12B show a different kind of threaded element, as an alternative means of providing securement of the device 10, without the ability to make significant fine adjustments in the amount of compression. A bolt 70 is shown, to be used in the housing 82 of the strap 80 instead of an adjustment screw 60. The advantage of this embodiment is enhanced simplicity of use. The bolt 70 includes a bolt thread 67, a non-threaded spine 68, and, similar to the adjustment screw 60, bolt 70 further includes a shaft 62, stop ring 64, and a retention knob 65. Located at the wide end of the spine is a quick-release tab 69. Those of skill in the art will appreciate that the bolt described and illustrated herein represents only one of many alternative embodiments contemplated as being within the spirit and scope of the invention.

A preferred embodiment of the device 10 includes a strap 80, a screw 60, and a compression pad 20. The strap 80 includes a housing 82, a tip 85, a top surface 86, and a bottom surface 89. The housing 82 includes an ulnar pad 40 that faces towards the ulnar surface of the wrist 100 when device 10 is applied to a patient. The housing 82 further includes a strap-tip exit opening 83, a spring guide 87, a spring hinge 88, a screw retention hole 90, a strap-tip insertion opening 91 and a cutout 94. The top surface 86 has strap threads 81 formed onto it. Each of the strap threads 81 has a concave notch 93 at its center. The tip 85 may optionally include a downward deflection as part of its structure to more easily enable the strap 80 to be pulled through the housing 82 and exit opening 83 without being impeded by aspects of the screw 60, for example the knob 61. The strap 80 can be formed of a material that has the properties of flexibility and shear strength, since flexibility is needed for it to be twisted, flexed or deflected so as to fit around a wrist 100, and since shear strength is needed to enable it to withstand the tension incurred during deployment. Examples of such a material can include, but are not limited to, a polypropylene or other plastic, or a nylon or a woven synthetic or natural material. The spring hinge 88, when the strap 80 is formed of a material generally of the types herein described, thus functions as a live hinge.

The adjustment screw 60, which is a threaded element, includes a knob 61, a shaft 62, a screw thread 63 that has a top end 63a and bottom end 63b, a stop ring 64, and a retention knob 65. The screw 60 fits into the spring guide 87, where it is retained with the shaft 62 being held inside the retention hole 90 between the stop ring 64 and the retention knob 65, and with the outside edges 66 of the screw threads 63 in contact with an interior sidewall of the spring guide 87. Each of the screw threads 63 may optionally have an outside edge 66a that can be angled to provide a flat surface to bear against the interior sidewall of the spring guide 87 and top surface 86 of the strap 80. The retention hole 90 accepts the retention knob 65 of the screw 60 by virtue of the resilience of the materials used to construct the housing 82 and the tapered shape of the retention knob 65. The length of the shaft 62 between the stop ring 64 and retention knob 65 may be greater than the thickness of the sidewall surrounding the retention hole 90 to permit limited travel of the screw 60 along its longitudinal axis. The screw 60 can be formed of any rigid material and examples including, but not limited to, a metal or a glass-filled nylon or a polycarbonate or other rigid natural or synthetic substance may be preferred.

The screw threads 63 may further include a taper along its outside diameter extending as much as from the top end 63a to the bottom end 63b, the taper having an angle of between approximately 0.01 degrees and approximately 45 degrees, more particularly between approximately 1 degree and approximately 15 degrees, the wider portion of the taper occurring at the top end 63a and the narrower portion occurring at the bottom end 63b. The interior sidewall of the spring guide 87 has a shape which matches the shape of the outside diameter of the screw threads 63; more particularly, a taper, if any, on the screw threads 63 shall be similarly present in the shape of the interior sidewall of the spring guide 87 so that the screw threads 63 may fit snugly within the spring guide 87. Further, the outside edge 66a of the screw threads 63 may be truncated, so as to provide each screw thread 63 a flat surface, instead of a sharp edge, with which to bear against the interior sidewall of the spring guide 87 and the top surface 86 of the strap 80 between the strap threads 81. In this embodiment a double-helical thread shape with truncated outer and inner edges 66a, 66b is used for the screw threads 63, although it must be appreciated by those skilled in the art that different thread shapes may also be used for this purpose.

The screw 60 may be able to move longitudinally within the spring guide 87 because the length of shaft 62 between the stop ring 64 and retention knob 65 may be greater than the thickness of the sidewall surrounding the screw retention hole 90. As the strap 80 is pulled through the housing 82, as when being tightened around a wrist 100, the motion of the strap 80 pulls the screw 60, by virtue of the contact between the strap threads 81 and screw threads 63, in the same direction. The taper of the screw threads 63 generally removes the screw threads 63 from contact with the interior sidewall of the spring guide 87, and together with the longitudinal movement of the screw 60 reduces resistance to the motion of the strap 80 being pulled through the housing 82. The strap threads 81 traverse across the screw threads 63, the resistance to this travel being further reduced by the concave notch 93 in the strap threads 81. Further, the entire spring guide 87 will flex along its arcuate axis 92 as the screw threads 63 pass over the strap threads 81 because of the flexion provided by the spring hinge 88. This permits a ratcheting type of motion of the strap 80 moving through the housing 82 due to the screw threads 63 engaging with the strap threads 81 thus permitting rapid tightening and securement of the device 10.

When the strap 80 has been suitably and fittingly (e.g. snugly) pulled through the housing 82 and the device 10 is under compression as when tightened around a wrist 100, the screw threads 63 engage strap threads 81 thereby preventing movement relative to each other. In this state, tension on the strap 80 increases and forces the screw threads 63 against the interior sidewall of the spring guide 87, in turn preventing further movement of the strap 80 because the screw threads 63 trap the strap threads 81. Because of their tapers, the screw threads 63 bear against the interior sidewall of the spring guide 87 to provide frictional resistance to both rotational and longitudinal motion of the screw 60 before the stop ring 64 bottoms out against the interior sidewall surrounding the screw retention hole 90. As tension increases, to a point, friction of the screw threads 63 against the interior sidewall of the spring guide 87 increases, providing additional securement of the device 10 around the wrist 100. Thus, by fitting the taper of the screw threads 63 to the taper of the interior wall of spring guide 87 so as to provide rotational friction with which to lock the tapered surfaces of the screw 60 and interior sidewall of the spring guide 87 together, the strap 80 is fastened. Alternatively, the screw threads 63 and the interior sidewall of spring guide 87 may have no taper, so that, for example, their shapes, instead of being tapered, may be generally cylindrical.

The compression pad 20 has loops 22 which permit the strap 80 to fit within the strap openings 23 formed by the loops 22, allowing the compression pad 60 to slide along the length of the strap 80. The openings formed by the loops in accordance with one embodiment of the invention are dimensioned in width and height as detailed elsewhere herein. The compression pad 20 further includes a notch 21, a compression surface 24 on the bottom, lateral sidewalls 25, and end sidewalls 26. The compression surface 24 is placed directly over the puncture site 106 and blood vessel 102 so as to reduce or halt blood flow 108 by occluding the vessel to permit a clot to form at the arteriotomy. The notch 21 helps the user position the compression pad 20 in the proper location over the puncture site 106 by providing a guide within which the cannula may slide during its removal from the blood vessel 102. In an alternative embodiment, the compression surface 24A is placed proximal to the puncture site 106 in the blood vessel 102 with the notch 21A enabling visual and physical access to the puncture site 106. The compression surface 24A, when the device 10 is under compression, thus partially or completely blocks the flow of blood 108.

The ulnar pad 40 on the housing 82 has ulnar surfaces 43 which are placed directly against the ulnar surface of the wrist 100, serving both as a cushion and, with the height A 44 in conjunction with the height of the compression pad 20, provides standoff to enable a space 105 to exist between the strap 80 and the surface of the wrist 100, thereby enabling blood flow through the ulnar artery 101 and veins 103 during compression of the blood vessel 102, in this example the radial artery. The tail 41 of the ulnar pad provides a barrier to prevent a patient's skin and hair from being caught in the insertion opening 91 (refer briefly to FIGS. 5 and 9). The ulnar pad 40 optionally can include a padding material attached to its surface to provide cushioning and thus greater comfort to the person wearing the device 10.

Examples of materials from which the compression pad 20 can be formed include polypropylene, polyester, nylon, or other thermoplastics, metals, or fibrous materials, or any other suitable material. It will be appreciated by those skilled in the art that a variety of materials and shapes of the pads, in addition to those disclosed and illustrated herein, may be employed and that alternatively, these pads may be integrally formed as non-separable parts of the strap 80. The compression surface 24 optionally can include a coating, or padding, gauze, sponge, hemostatic material, or other suitable and useful material attached to or integrally formed with it. All such alternative compression pad embodiments are contemplated as being within the spirit and scope of the invention.

The device 10 is secured around a wrist 100 by threading the tip 85 through the insertion opening 91 and pushing it through the housing 82 and pulling it through the strap-tip exit opening 83. The screw threads 63 of the screw 60, which is retained inside the spring guide 87, engage with the strap threads 81 and secure it in place within the housing 82.

When the strap 80 is pulled tight, the screw 60 is pulled in the direction that the strap is moving by friction of the strap threads 81 against the screw threads 63 and moves to the extent permitted by the length of the shaft 62, between the stop ring 64 and retention knob 65, contained inside the screw retention hole 90.

When the user stops pulling the strap 80 through the housing 82, the compression of the device 10 against the circumference of the wrist 100 causes the screw 60, while its screw threads 63 are still engaged with the strap threads 81, to move towards the bottom of the spring guide 87 until stopped by the screw threads 63 coming into contact with the interior sidewall of the spring guide 87. This provides a securement means, which permits a user to quickly tighten the device 10 and fasten it at the circumference to which it has been tightened. The securement enabled by a taper included in the shape of the screw threads 63 and the interior sidewall of the spring guide 87 has been described previously herein.

In addition to providing rapid securement, the screw threads 63 engaging with the strap threads 81 provide an adjustment means to enable very gradual adjustment of the circumference of the fastened device 10 around the wrist 100. A user, by twisting the knob 61 causes the screw threads 63 to move against the strap threads 81 thereby moving the strap 80 relative to the housing 82. This is done without effecting any inadvertent release of securement of the device 10.

Thus, a securement means integrated with an adjustment means is created by the screw threads 63 located on the screw 60, which is retained in the spring guide 87, engaging with the strap threads 81. The strap 80, specifically that portion extending from the exit opening 83, is pulled through the housing 82 by the user, which action causes the concave notches 93 in the centers of the strap threads 81 to travel over the screw threads 63, thereby permitting movement of the strap 80 through the housing 82. Flexion along the arcuate axis 92 of the spring hinge 88 provides sufficient space to allow movement of the strap 80 when the edge of a screw thread 63 is directly over the concave notch 93 of the strap thread 81. This is further assisted by the angle of the screw thread 63. Said flexion further causes the spring hinge 88 to move to its original position when the outer edge 66a of a screw thread 63 passes over the concave notch 93 of a strap thread 81 coming to a rest against the top surface 86 of the strap 80 as shown in FIGS. 11A and 11B, thereby securing the strap 80 at the desired circumference around the wrist 100.

A release means feature is provided in the device 10. A rapid release of the strap 80 through the housing 82 may be achieved by flexing the spring hinge 88 along its arcuate axis 92 and pulling on the portion of the strap 80 extending from the insertion opening 91 of the housing 82. A user may flex the spring hinge 88, as in the manner of a live hinge, by leveraging the knob-end of the screw 60 along its arcuate axis 92, which causes it to move against the adjacent interior sidewall of the spring guide 87 in which it is inserted. The spring guide 87 is moved away from the top surface 86 of the strap 80, such action disengaging the screw threads 63 from the strap threads 81 and top surface 86 thus permitting the strap 80 to move freely within the housing 82.

Thus, a rapid release means is created when the user moves the screw 60 to deflect the spring guide 87 away from the strap 80 contained in the housing 82, such deflection permitted by the flexion of the spring hinge 88 thereby acting as the fulcrum, the screw 60 thereby acting as a lever. It may be seen then that pulling the screw 60 away from the strap 80 and perpendicularly to its longitudinal axis causes it to act as a lever to flex open the hinge means, in the form of the spring hinge 88, thereby decoupling the threads 81 on the strap 80 from the threads 63 on the screw 60, to enable slidable withdrawal of the strap 80 out of the housing 82, thereby providing a release means of the device 10.

An alternative embodiment of the device 10 includes a bolt 70 which is placed inside the housing 82 instead of the adjustment screw 60 so that the spine 68 is in contact with the interior sidewall of the spring guide 87 and the bolt threads 67 are in contact with the strap threads 81. The bolt 70 provides a fastening means, but without the compression adjustment enabled by the screw 60. The bolt 70 is fastened in the housing 82 by means of the shaft 62 being inside the screw retention hole 90, the retention knob 65 on the outside and the stop ring 64 on the inside. Though fastened in the housing 82, the bolt 70 may move freely around its longitudinal axis, and to the extent the length of the shaft 62 between the stop ring 64 and retention knob 65 is longer than the thickness of the sidewall surrounding the screw retention hole 90, along its longitudinal axis. The bolt 70 thus generally provides a securement means similar to that of the adjustment screw 60, which is described elsewhere herein, but does not provide the adjustment features to the same extent as the adjustment screw 60. In this embodiment, the bolt 70 has a tapered shape, similar to an embodiment of the adjustment screw 60 previously described, though a non-tapered shape would suffice, for example a cylindrical shape.

A rapid release of the strap 80 through the housing 82 may be achieved by flexing the spring hinge 88 along its arcuate axis 92 and pulling on the portion of the strap 80 extending from the insertion opening 91 of the housing 82, in a fashion described above with the adjustment screw 60 in place. With the bolt 70 in place, the rapid release is achieved in a similar fashion, except that the user pushes on the quick-release tab 69 towards the spring hinge, thereby lifting the bolt 70, thus flexing the spring hinge 88 in its vertical axis 92 by means of the spine 68 bearing against the interior sidewall of the spring guide 87. Alternatively, the bolt 70 may be rotated around its longitudinal axis, to expose the non-threaded spine 68 to the strap threads 81 thereby disengaging from them and allowing the strap 80 to move freely within the housing 82. Such rotation may be effected by pushing on the quick-release tab 69 from side to side. Thus the bolt 70 used as an alternative to the adjustment screw 60 provides a securement means and a release means, but does not provide a means of making fine adjustments without release of the securement means.

A method of using the device of the present invention includes the following steps:
i) Placing the compression surface 24 on the wrist 100. A user fits the device 10 around a wrist 100 of a patient and by pulling the tip 85 through the housing 82, fastens it loosely so that the compression pad 20 may be moved to the desired point overlying the blood vessel 102, for example a radial artery. The method provides that the device 10 need not necessarily be pulled tight initially, and this first step serves to place and keep in place the compression surface 24 of the compression pad 20 in the correct position relative to the puncture site 106, in which the cannula or needle is still located.

ii) Tightening the device 10 while pulling out the cannula. The user pulls out the cannula or needle from the puncture site 106 and simultaneously pulls the tip 85 of the strap 80 with their hand while holding the housing 82 or knob 61 in place with their thumb, such that flow of blood from the puncture site 106 is stopped. Alternatively a second person may pull out the cannula as the user pulls the tip 85 with one hand while holding the housing 82 in place with their other hand, or the user may press down on top of the compression pad 20 forcefully to compress the blood vessel 102 while removing the cannula, and then after discarding the cannula while continuing to press down onto the compression pad 20, pulls the tip 85 in the fashion described above.

iii) Adjusting the amount of compression applied to the surface of the wrist 100. The user, by twisting the knob 61, may tighten or loosen the device 10 to adjust the amount of compression applied to the surface of the wrist 100, for example, when adjusting compression so that the blood vessel 102 retains a degree of patency during the compression period while hemostasis occurs at the puncture site 106. Compression may further be gradually reduced during the period in which hemostasis occurs to help avoid complications.

iv) Releasing the device 10 from the wrist 100. The user, by tilting the screw 60 away from the strap 80, disengages the screw threads 63 from the strap threads 81 enabling the user to pull the strap 80 through the housing 82 to release the device 10 from the wrist 100 of the patient, and can then remove the device 10 entirely.

It will be understood that the present invention is not limited to the method or detail of construction, fabrication, material, application or use described and illustrated herein. Indeed, any suitable variation of fabrication, use, or application is contemplated as an alternative embodiment, and thus is within the spirit and scope of the invention. Accordingly, while the present invention has been shown and described with reference to the foregoing embodiments of the invented apparatus and method of use, it will be apparent to those skilled in the art that other changes in form and detail may be made therein without departing from the spirit and scope of the invention as defined in the claims.

It is further intended that any other embodiments of the present invention that result from any changes in application or method of use or operation, configuration, method of manufacture, shape, size, or material, which are not specified within the detailed written description or illustrations contained herein yet would be understood by one skilled in the art, are within the scope of the present invention.

We claim:

1. A mechanism for securing and adjusting an adjustable vascular compression device that includes at least a strap, a housing attached to said strap, and an adjustment screw, wherein:
the housing further includes at least a spring hinge and a spring guide, the spring hinge being formed of a material to permit flexion in the manner of a live hinge;
the strap further includes strap threads located on a top surface of the strap, said strap threads having a concave notch in their centers;
a tip of the strap opposite the housing can be inserted into the housing and the strap can be slidably moved through the housing;
the adjustment screw further includes screw threads, the screw threads having a double-helical thread shape and a top end and a bottom end, the top end having a diameter larger than the bottom end;
the adjustment screw is secured into the spring guide where it can be rotated;
the screw threads engage with the strap threads and interior of the spring guide under tension, thereby securing the vascular compression device in place and permitting adjustment of the compression applied by slidable movement of the strap through the housing when the adjustment screw is rotated, the screw threads passing over the concave notches in the strap threads;
the spring hinge flexes to permit the adjustment screw, when said adjustment screw is moved in an arcuate axis, to move away from the strap thereby disengaging the screw threads from the strap threads.

2. The device of claim 1, the screw threads of which more particularly include a truncated edge that bears against the interior sidewall of the spring guide.

3. A vascular compression device for partially or completely occluding blood flow in a single blood vessel by means of adjustably applying compression to said vessel, the device including at least:
a strap having two ends, a housing placed at one end of the strap, and strap threads on a top surface of the strap;
an adjustment screw inserted in the housing, screw threads on which engage the strap threads on the top surface of the strap, and,
one compression pad that is attached to the strap, is slidably movable along the strap's length whereby a compression surface of the compression pad can be positioned over a single blood vessel and puncture site, and is dimensioned so as to provide a space between the strap and the body surface to allow substantial compression to be applied to said single blood vessel without such compression concomitantly applied to blood vessels not positioned under the compression pad; wherein,
the strap threads on the top surface of the strap each have a concave notch in their centers;
the housing includes a spring guide and a spring hinge, the spring hinge formed of a flexible material which permits its operation in the manner of a live hinge;
a tip of the strap opposite the housing can be inserted into the housing and the strap can be slidably moved through the housing;
the screw is assembled into the spring guide where it can be rotated;
the adjustment screw threads have a double-helical thread shape, and a top end and a bottom end, the top end having a diameter larger than the bottom end;
the screw threads engage with the strap threads and interior of the spring guide under tension, thereby securing the device in place;
the adjustment screw can be rotated when the strap is inserted into the housing, the screw threads engaging with the strap threads and interior of the spring guide under tension, thus causing slidable movement of the strap through the housing to increase or decrease circumference of the strap thereby increasing or decreasing compressive force exerted by the strap through the compression surface of the compression pad;

the spring hinge flexes to permit the adjustment screw, when said adjustment screw is moved in an arcuate axis, to move away from the strap, thereby disengaging the screw threads from the strap threads.

4. The device of claim 3, the screw threads of which more particularly include a truncated edge that bears against the interior sidewall of the spring guide.

5. The device of claim 3, the compression pad of which further includes at least one notch at an end of the compression surface to provide visual and physical access to a puncture site and permit withdrawal of a cannula from the puncture site.

6. The device of claim 3, the compression pad of which more particularly has a height of between 0.25 and 5.0 centimeters.

* * * * *